US007229652B2

(12) United States Patent
Yuan et al.

(10) Patent No.: US 7,229,652 B2
(45) Date of Patent: Jun. 12, 2007

(54) **EXTRACT FROM THE LEAVES OF *TOONA SINENSIS* ROEM., AND THE PREPARATION PROCESS AND USES THEREOF**

(75) Inventors: Shyng-Shiou Yuan, Kaohsiung (TW); Hseng-Kuang Hsu, Kaohsiung (TW); Yi-Chen Chia, Pingtung County (TW)

(73) Assignee: Kaohsiung Medical University, Kaoshiung (TW)

( * ) Notice: Subject to any disclaimer, the term of this patent is extended or adjusted under 35 U.S.C. 154(b) by 219 days.

(21) Appl. No.: 10/785,444

(22) Filed: Feb. 23, 2004

(65) Prior Publication Data

US 2005/0186297 A1 Aug. 25, 2005

(51) Int. Cl.
*A61K 36/00* (2006.01)
(52) U.S. Cl. ...................... 424/774; 424/725
(58) Field of Classification Search .................... None
See application file for complete search history.

(56) References Cited

U.S. PATENT DOCUMENTS

| | | | | | |
|---|---|---|---|---|---|
| 5,602,184 | A | * | 2/1997 | Myers et al. | 514/739 |
| 6,530,453 | B1 | * | 3/2003 | Miura et al. | 181/292 |
| 2002/0132021 | A1 | * | 9/2002 | Raskin et al. | 424/773 |
| 2002/0187957 | A1 | * | 12/2002 | Halstead | 514/50 |

FOREIGN PATENT DOCUMENTS

| CN | 1454615 | * | 11/2003 |
|---|---|---|---|
| JP | 02083310 | * | 3/1990 |

OTHER PUBLICATIONS

Hsu et al. Kaohsiung J. Med. Sci. 2003. vol. 19, No. 8, pp. 385-389.*
Luo et al. Fitoterapia. 2000. vol. 71, pp. 492-496.*
Green, J. The Herbal Medicine-Maker's Handbook, A Home Manual. 2000 The Crossing Press.*
Grewal, P.S. Revue de Nematologie. 1989. vol. 12, No. 3, pp. 317-322.*
Edmonds, et al., "*Toona Sinensis* (*Meliaceae*)", Curtis's Botanical Magazine, 15(3), pp. 186-193, 1998.
Xia-Dong Luo, et al., "Limonoids and phytol derivatives from *Cedrela sinensis*", Fitoterapia, 71, 492-496, 2000.
Jong-Cheol Park, et al., "Phenolic Compounds from the Rachis of *Cedrela sinensis*", Kor. J. Pharmacogn. 27(3), pp. 219-223, 1996.
Si-Ming Yu, et al., Journal of Anhui University Natural Science Edition No. 4, pp. 91-94, 1990.
Yue-Zhen Liu et al., Hebei Forestry Technology, No. 4, pp. 51-52, Dec. 1997.
Wang, et al., "*Toona Sinensis* Increases Glut4 Glucose Transporter Protein In Adipose Tissue From Alloxan-Induced Diabetic Rats", Annual Conference of Biomedical Science, p. 198, 2001.
Hai-Chiu Chang, et al., "Extract From The Leaves of *Toona Sinensis* Roemor Experts Potent Antiproliferative Effect on Human Lung Cancer Cells", The American Journal of Chinese Medicine, vol. 30, Nos. 2 & 3, 307-314.
Hui-Chiu Chang, et al.; "Extract from the Leaves of *Toona sinensis* Roemor Exerts Potent Antiproliferative Effect on Human Lung Cancer Cells"; The American Journal of Chinese Medicine, vol. 30, Nos. 2 & 3, pp. 307-314; © 2002 World Scientific Publishing Company & Institute for Advanced Research in Asian Science and Medicine.
Hui-Chiu Chang, et al.; "Effects of Chinese Herbal Prescriptions on Copulatory Activity in Aged Male Rats: A Preliminary Study"; American Journal of Chinese Medicine, vol. XXVI, No. 1, pp. 83-90; © Instiute for Advanced Research in Asian Science and Medicine.
Chi-Feng Liu, et al.; "Cytoprotection by Propolis Ethanol Extract of Acute Absolute Ethanol-Induced Gastric Mucosal Lesions"; The American Journal of Chinese Medicine, vol. 30, Nos. 2 & 3, pp. 245-254; © 2002 World Scientific Publishing Company & Institute for Advanced Research in Asian Science and Medicine.
Youichi Shinozaki, et al.; "Dantaxusins C and D, Two Novel Taxoids from *Taxus yunnanensis* "; j. Nat. Prod. 2002, 65, pp. 371-374; © 2002 American Chemical Society and American Society of Pharmacognosy, Published on Web Feb. 8, 2002.
Michael Thomsen, "herb focus turmeric"; phytomedicine, © Phytomedicine.
Ivor Hughes, "Herbs in Africa. Extraction Products, The Home Based Herbal Business, Part 6"; SIA6 Extraction Products, 4 pgs.; Science in Africa, © 2002 Herbdaia, New Zealand.

* cited by examiner

*Primary Examiner*—Christopher R. Tate
(74) *Attorney, Agent, or Firm*—The Webb Law Firm

(57) ABSTRACT

Disclosed are extracts from the leaves of *Toona sinensis* Roem. prepared by extracting the leaves of *Toona sinensis* Roem. using water and an alcohol in sequence. Also disclosed are processes for preparing extracts from the leaves of *Toona sinensis* Roem., and uses of such extracts in the manufacture of medicaments for use in the treatment of ovarian cancer and/or bladder cancer.

17 Claims, 7 Drawing Sheets

SKOV3 control 1 mg/ml

100 μg/ml

PA-1 control 1 mg/ml

10 μg/ml

EXTRACT FROM THE LEAVES OF *TOONA SINENSIS* ROEM., AND THE PREPARATION PROCESS AND USES THEREOF

BACKGROUND OF THE INVENTION

1. Field of the Invention

The invention relates to an extract from the leaves of *Toona sinensis* Roem., a process of preparing the extract, and uses of the extract in the treatment of ovarian and/or bladder cancer.

2. Description of the Related Art

*Toona sinensis* Roem. or *Cedrela sinensis*, commonly known as Chinese mahogany cedar or Chinese *Toona*, is a perennial deciduous tree of the family Meliaceae. Its bark is reddish brown. Its tender leaves are edible and are available for picking almost all year around. Originally grown in the south-eastern part, the south-western part and the northern part of China, *Toona sinensis* is now being planted in many countries. (Jennifer M. Edmonds and Martin Staniforth, *TOONA SINENSIS (Meliaceae)*, Curtis's Botanical magazine, 15 (3), 186–193, 1998; Xiao-Dong Luo et al., *Fitoterapia*, 71, 492–496, 2000; Jong-Cheol Park et al., *Kor. J. Pharmacogn*, 27(3), 219–223, 1996).

Because the entire tree of *Toona sinensis* is useful, it has high economic value. According to reports, almost every part of *Toona sinensis*, including seeds, bark, root bark, petioles, and leaves, has a medicinal effect (Jennifer M. Edmonds and Martin Staniforth, 1998, supra; Jong-Cheol Park et al., 1996, supra).

Seeds of *Toona sinensis* contain oil, which is colorless and fragrant and can be used as edible oil. Shoots and leaves of *Toona sinensis* are rich in carotene, amino acids and vitamins, and are therefore quite popular as a vegetable. In addition, mellowed leaves can be used as animal fodder.

According to literatures (Jennifer M. Edmonds and Martin Staniforth, 1998 supra; Xiao-Dong Luo et al., 2000, supra) the bark, root bark and seeds of *Toona sinensis* are useful in the treatment of neuralgia, duodenal ulcer, stomach upsets, gonorrhea, menstrual disorder, ascariasis, rheumatoid arthritis, and cancer, and are useful as an astringent, a carminative, an analgesic, and in suppressing growth of typhoid bacillus and amoeba protozoa (Si-Ming Yu and Ze-Dang Zhang, Journal of Anhui University Natural Science Edition No. 4, 91–94, 1990; Yue-Zhen Liu and Yu-Ping Li, Hebei Forestry Technology, No. 4, 51–52, Dec. 1997).

According to literatures, leaves of *Toona sinensis* have anti-inflammatory, antidoting and worm-killing effects, and are useful for treating enteritis, dysentery, carbuncles, boils, dermatitis rhus, scabies, and tinea blanca, as well as for improving body health. In addition, aqueous extracts of leaves of *Toona sinensis* have been used as a folk medicine for improving hypertension and diabetes. Hseng-Kuang Hsu et al. found that aqueous extracts of *Toona sinensis* leaves are capable of lowering blood sugar in alloxan-induced diabetic rats (Wang PH et al., *Toona sinensis* increase GLUT4 glucose transporter protein in adipose tissue from Alloxan-induced diabetic rats, Annual Conference of Biomedical Science, p. 198, 2001). In another study, it was found that aqueous extracts from leaves of *Toona sinensis* are capable of suppressing proliferation of human lung adenocarcinoma cells A549 (Hui-Chiu Chang et al. (2002), American Journal of Chinese Medicine, Vol. 30, Nos. 2 & 3, 307–314).

In the other aspects, leaves of *Toona sinensis* are used as a dyeing agent or glaze.

In addition, as the wood of *Toona sinensis* is hardy, delicate, and resistant to warping, cracking and moisture, it is often used as timber for high-grade furniture, shipbuilding, bridge construction, etc. It is also used in the making of bats for table-tennis, rackets for badminton and tennis, and musical instruments.

*Toona sinensis* is also a good species for forestation to prevent landslides. In addition, *Toona sinensis* oil can be extracted from the wood of *Toona sinensis* to be used as an aroma enhancer for cigars.

To the inventors' knowledge, no literature or prior patent application has taught or suggested that the leaves of *Toona sinensis* or extracts from the leaves of Toona sinensis have activity in suppressing growth of ovarian cancer cells, and are therefore useful in the preparation of medicaments for the treatment of ovarian cancer.

SUMMARY OF THE INVENTION

Therefore, in one aspect, the present invention provides an extract from the leaves of *Toona sinensis*, which is prepared by the process including the following steps:
(1) extracting the leaves of *Toona sinensis* with water by heating to obtain a water-extracted first extract; and
(2) extracting the water-extracted first extract obtained in step (1) with an alcohol to obtain an alcohol-extracted second extract.

In another aspect, the present invention provides a process for preparing an extract from leaves of *Toona sinensis*, comprising the following steps:
(a) extracting the leaves of *Toona sinensis* with water by heating to obtain an aqueous extract solution;
(b) drying the aqueous extract solution in step (a) to obtain a dried first extract;
(c) dissolving the first extract obtained in step (b) in an alcohol solvent to form an alcohol extract solution; and
(d) removing the alcohol solvent from the alcohol extract solution obtained in step (c) to obtain a dried second extract.

The extract from the leaves of *Toona sinensis* according to the present invention has been proven to be effective in inhibiting growth of ovarian cancer cells (particularly SKOV3 and PA-1). Therefore, in still another aspect, the present invention provides a pharmaceutical composition, which includes the aforesaid extract from the leaves of *Toona sinensis* in an amount capable of effectively inhibiting the growth of ovarian cancer cells.

BRIEF DESCRIPTION OF THE DRAWINGS

Other features and advantages of this invention will become apparent in the following detailed description of the preferred embodiment with reference to the accompanying drawings, in which.

DETAILED DESCRIPTION OF THE PREFERRED EMBODIMENTS

Figure 1:
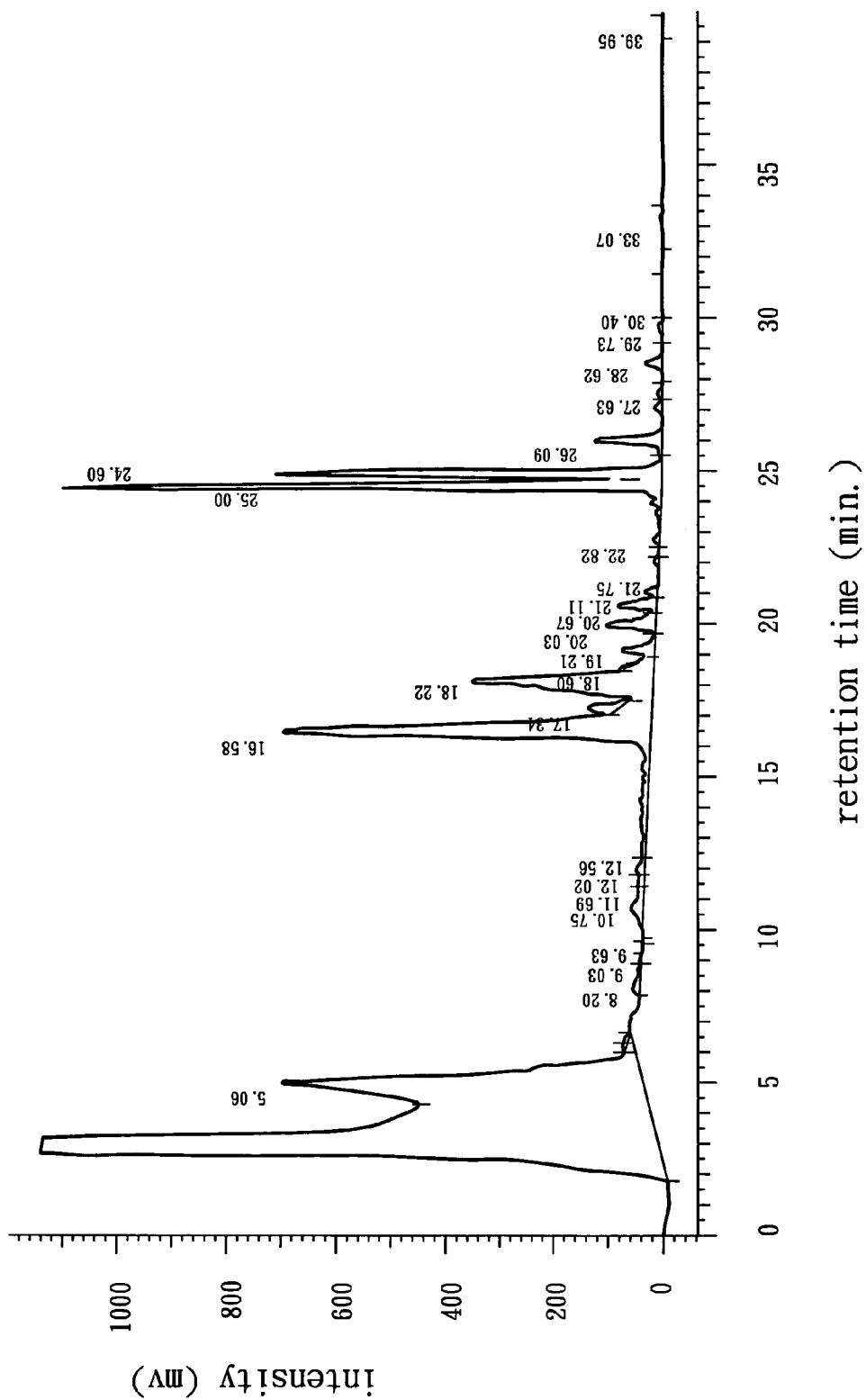
FIG. 1 is an HPLC elution profile of a product (i.e., "TS 5-4" obtained in Example 1 below) extracted from the leaves of *Toona sinensis* with water.

In a study headed by Dr. Hseng-Kuang Hsu (Hui-Chiu Chang et al. (2002), American Journal of Chinese Medicine, Vol. 30, Nos. 2 & 3, 307–314), a crude aqueous extract of *Toona sinensis* was prepared using a method described in Hui-Chiu Chang et al., Am. J. Chin. Med., 30: 307–314. According to the study, 100 g of leaves were added to 1000 ml of water, which was heated until only 100 ml of the solution remained. The solution was then centrifuged at 1000×g for 20 minutes to obtain a supernatant for experimentation purposes.

Experiments showed that the aqueous extract from the leaves of *Toona sinensis* could inhibit expression of cyclin D1 and cyclin E of human adenocarcinoma cells A549 and was thus effective in blocking cell cycle progression of the human adenocarcinoma cells A549.

The inventors also made other attempts to obtain extracts from the leaves of *Toona sinensis* using various processing methods, and finally obtained an extract from the leaves of *Toona sinensis*, which was prepared using a process that included the following steps:

(1) extracting the leaves of *Toona sinensis* with water by heating so as to obtain a water-extracted first extract, and (2) extracting the water-extracted first extract obtained in step (1) with alcohol so as to obtain an alcohol-extracted second extract.

Accordingly, this invention also provides a process for preparing an extract from the leaves of *Toona sinensis*, which includes the following steps:

(a) extracting the leaves of *Toona sinensis* with water by heating so as to obtain an aqueous extract solution;

(b) drying the aqueous extract solution obtained in step (a) so as to obtain a dried first extract;

(c) dissolving the first extract obtained in step (b) in an alcohol solvent so as to form an alcohol extract solution; and (d) removing the alcohol solvent from the alcohol extract solution obtained in step (c) to obtain a dried second extract.

Preferably, in step (a) of the process according to this invention, the aqueous extract solution is obtained by heating and boiling down the water to which the leaves of *Toona sinensis* were added to an appropriate amount for subsequent filtration. Filtration may be conducted by using gauze, cotton wool or a filter sieve with a predetermined mesh. In a preferred embodiment of this invention, filtration is conducted using gauze and cotton. In another preferred embodiment of this invention, filtration is conducted using a 70-mesh filter sieve.

Preferably, steps (b) to (d) of the process according to this invention are carried out under low-temperature conditions so that damage to active components of the leaves of *Toona sinensis* can be minimized.

Preferably, the drying treatment conducted in step (b) of the process according to this invention is selected from the group consisting of lyophilization, low-temperature spray-drying, low-temperature evaporation, and a combination thereof. In a preferred embodiment of this invention, the drying treatment conducted in step (b) is lyophilization.

Preferably, step (b) of the process according to this invention includes the following processing steps:

(i) centrifuging the aqueous extract solution obtained in step (a) to give a supernatant and a precipitate; and (ii) subjecting the supernatant obtained in step (i) to a drying treatment.

Preferably, in step (i), the step of centrifuging the aqueous extract solution obtained in step (b) is carried out at 3000 rpm and at a low temperature (e.g., 4° C.).

Preferably, the drying treatment used in step (ii) is selected from the group consisting of lyophilization, low-temperature spray-drying, low-temperature evaporation, and a combination thereof. In a preferred embodiment of this invention, the drying treatment used in step (i) is lyophilization.

In addition, the precipitate obtained in step (i) may be dried in a similar manner to produce a dried product.

Preferably, the removal of the alcohol solvent in step (d) is conducted using a treatment selected from the group consisting of evaporation, lyophilization, spray-drying, and a combination thereof. In a preferred embodiment of this invention, step (d) is conducted using lyophilization.

Preferably, in step (d) of the process according to this invention, prior to removal of the alcohol solvent, the alcohol extract solution obtained in step (c) may be filtered or centrifuged so as to remove any insoluble substance contained therein. More preferably, in step (d) the alcohol extract solution obtained in step (c) is centrifuged at 3000 rpm and 4° C. for 12 minutes before proceeding with the removal of the alcohol solvent.

Alcohols applicable for use in step (c) of the process according to this invention include, for instance, ethanol, methanol, propanol, isopropanol, n-butanol, isobutanol or a combination thereof. In a preferred embodiment of this invention, the alcohol used in step (c) of the process according to this invention is ethanol.

As shown in Example 1, to be described hereinbelow, the first extract obtained according to step (b) of the process and the second extract obtained according to step (d) of the process were sampled for HPLC analysis, and it was proven that the peaks of major compounds of these two extracts were indeed different.

The inventors also attempted to carry out further extraction of the second extract obtained in step (d) of the process, which included the following steps:

(i) dissolving the second extract in 50% ethanol; centrifuging the solution to give a supernatant portion and a precipitate portion; and lyophilizing the supernatant portion and the precipitate portion, respectively, to obtain a dried third extract from the supernatant portion and a fourth extract from the precipitate portion;

(ii) dissolving the fourth extract obtained in step (i) in 25% ethanol; centrifuging the solution to give a supernatant portion and a precipitate portion; lyophilizing the supernatant portion and the precipitate portion, respectively, to obtain a dried fifth extract from the supernatant portion and a sixth extract from the precipitate portion;

(iii) dissolving the sixth extract obtained in step (ii) in RO water; centrifuging the solution to give a supernatant portion and a precipitate portion; lyophilizing the supernatant portion and the precipitate portion, respectively, to obtain a dried first RO water extract from the supernatant portion and a second RO water extract from the precipitate portion; and (iv) dissolving the second RO water extract obtained in step (iii) in RO water; centrifuging the solution to give a supernatant portion and a precipitate portion; and lyophilizing the supernatant portion and the precipitate portion, respectively, to obtain a dried third RO water extract from the supernatant portion and a fourth RO water extract from the precipitate portion.

In the aforesaid steps (i), (ii), (iii) and (iv), separation of the supernatant portion and the precipitate portion was accomplished by centrifugation at 3000 rpm and 4° C. for 12 minutes.

To investigate the bioactivity of the various extracts from the leaves of *Toona sinensis* thus obtained, the inventors studied the cytotoxicity of the extracts from the leaves of *Toona sinensis* using selected extracts to treat various types of cancer cells from the urogynecological system.

At first, the inventors used a bladder cancer cell line, T24, to conduct a preliminary anti-cancer cell activity screening, and found that the second extract obtained by using the process according to this invention had an optimum cancer cell growth inhibiting activity, the first extract obtained in step (b) of the process being second thereto.

The inventors further used the second extract to treat two ovarian cancer cell lines, SKOV3 and PA-1, two cervical cancer cell lines, HeLa and HeLaS3, and an endometrial cancer cell line, RL95-2. The inventors found that the second extract had a selective cytotoxicity on ovarian cancer cells. Therefore, it is also anticipated that the extracts from the leaves of *Toona sinensis* have application in the preparation of pharmaceutical compositions for treating ovarian cancer.

Accordingly, the present invention provides a pharmaceutical composition, comprising:

(a) a therapeutically effective amount of the second extract prepared by using the process according to this invention; and (b) a pharmaceutically acceptable carrier.

A pharmaceutical composition containing an extract of the leaves of *Toona sinensis* which is prepared by using the process according to this invention can be used to treat ovarian cancer or bladder cancer. Therefore, the extract of the leaves of *Toona sinensis* can be administered to a subject having ovarian or bladder cancer.

This invention further provides a pharmaceutical composition for treating bladder cancer, comprising:

(a) a therapeutically effective amount of an extract from the leaves of *Toona sinensis* selected from one of the following:
  (i) an extract obtained by extracting the leaves of *Toona sinensis* with water; and
  (ii) an extract obtained by sequentially extracting the leaves of *Toona sinensis* with water and an alcohol; and (b) a pharmaceutically acceptable carrier.

The term "pharmaceutically acceptable carrier" as used herein refers to carriers known in the art to be suitable for the manufacture of pharmaceuticals and including, but not limited to, water, normal saline, glycerin, organic solvents, stabilizers, chelating agents, preservatives, emulsifiers, suspending agents, diluents, gel-forming agents, liposomes, etc.

The pharmaceutical composition according to this invention may be prepared by a method known in the art into forms suitable for parenteral, oral or topical administration, including, but not limited to, injection, solution, capsule, dispersion, suspension, etc.

To produce an oral solid preparation, an excipient and, if necessary, a binder, a disintegrator, a lubricant, a coloring matter, a flavoring agent and/or the like may be admixed with an extract of this invention. The resultant mixture can then be formed into tablets, coated tablets, granules, powder, capsules or the like by a method known per se in the art. Such additives can be those generally employed in the present field of the art, including excipients: lactose, sucrose, sodium chloride, glucose, starch, calcium carbonate, kaolin, micro-crystalline cellulose, and silicic acid; binders: water, ethanol, propanol, sucrose solution, glucose solution, starch solution, gelatin solution, carboxymethylcellulose, hydroxypropylcellulose, hydroxypropylstarch, methyl-cellulose, ethylcellulose, shellac, calcium phosphate, and polyvinylpyrrolidone; disintegrators: dry starch, sodium alginate, powdered agar, sodium hydrogencarbonate, calcium carbonate, sodium lauryl sulfate, monoglycerol stearate, and lactose; lubricants: purified talc, stearate salts, borax, and polyethylene glycol; and corrigents: sucrose, bitter orange peel, citric acid, and tartaric acid.

To produce an oral liquid preparation, a flavoring agent, a buffer, a stabilizer and the like may be admixed with an extract of this invention. The resultant mixture can then be formed into a solution for internal use, a syrup, an elixir or the like by a method known per se in the art. In this case, the flavoring agent can be the same as that mentioned above. Illustrative of the buffer is sodium citrate, while illustrative of the stabilizer are tragacanth, gum arabic, and gelatin.

To prepare an injection, a pH regulator, a buffer, a stabilizer, an isotonicity and the like may be admixed with a compound of this invention. The resultant mixture can then be formed into a subcutaneous, intramuscular or intravenous injection by a method known per se in the art. Examples of the pH regulator and buffer include sodium citrate, sodium acetate, and sodium sulfate. Examples of the stabilizer include sodium pyrosulfite, EDTA, thioglycollic acid, and thiolactic acid. Examples of the isotonicity include sodium chloride and glucose.

Preferably, the pharmaceutical composition according to this invention is prepared into a form suitable for injection, such as powder injection, lyophilization product for injection, emulsion injection, oily injection, liposome injection, etc.

The term "effective amount" as used herein refers to an amount of a *Toona sinensis* leaf extract-containing pharmaceutical composition of this invention which is sufficient to provide a desired therapeutic effect when administered to a treated subject requiring the composition without causing undesirable severe damage to non-targeted tissues or organs. The therapeutically effective amount will change depending on different factors. These factors include, for instance, the type of disease or illness, the weight, age, physical condition and response of the subject to be treated, and the route of administration. It is noted that the therapeutically effective amount can be readily determined by a person skilled in the art.

The unit dosage form and the frequency of administration of the pharmaceutical composition according to this invention will vary depending on the following factors: the severity of the disease or illness to be treated, the route of administration, and the weight, age, physical condition and response of the subject to be treated. In general, the daily dosage of the pharmaceutical composition according to this invention is 0.67 mg to 6.7 mg per kilogram of the body weight of the subject to be treated, and can be administered in one or divided doses parenterally, orally or topically. Preferably, the pharmaceutical composition according to this invention is administered by intraperitoneal injection, continuous intravenous injection, topical arterial single injection, topical tumor direct injection, etc. In a preferred embodiment, the pharmaceutical composition according to this invention is administered by intraperitoneal injection or topical tumor direct injection.

The pharmaceutical composition according to the present invention can be administered daily. Preferably, the pharmaceutical composition is administered five consecutive days a week with two days of rest for a period of 43 days or until remission of symptoms.

The pharmaceutical composition according to the present invention can be administered alone, or in combination with other therapeutic methods or medicaments for use in the treatment of ovarian or bladder cancer. The therapeutic methods include chemotherapy and external beam radiation therapy. The therapeutic medicaments include, but are not limited to, paclitaxel, cisplatin, carboplatin, cyclophosphamide, and doxorubicin.

This invention will be described in detail with reference to the following examples, which are given for the purpose of illustration only and are not intended to limit the scope of this invention.

EXAMPLE 1

Preparation of Extracts from Leaves of *Toona sinensis*

The leaves of *Toona sinensis* used in this example were obtained from *Toona sinensis* Roem. grown in Tuku Chen, Yunlin Hsien, Taiwan.

Extraction Procedure A

Tender leaves of *Toona sinensis* were picked and washed briskly with water. A suitable amount of RO water was added to the leaves in a proportion of 4 liters of RO water to 1 kilogram of leaves. The mixture was heated to a boil and kept boiling for 30 minutes. Then, the leaves were removed, and the remainder was heated slowly to a concentrate, which was filtered with a filter sieve (70-mesh). The filtered concentrate was lyophilized using a Virtis apparatus to obtain a crude extract, which was called "TS 5-4" (also identified as "TSL-CE"). In general, 100 g of leaves can yield approximately 5–6 g of lyophilized powder using this procedure.

In addition, the filtered concentrate could be subjected to centrifugation prior to lyophilization. The filtered concentrate was centrifuged at 4° C. at 3000 rpm (Beckman Avanti™ J-30I) for 12 minutes to give a supernatant portion and a precipitate portion containing insoluble substances. The supernatant portion was subjected to lyophilization using a Virtis apparatus to obtain a lyophilized water extract, which was called "TSL-1".

Both "TS 5-4" and "TSL-1" belong to the aforesaid "water-extracted first extract". For the convenience of illustration, "TSL-1" was subjected to a further extraction procedure, which will be described hereinbelow.

Extraction Procedure B 50 g of extract "TSL-1" obtained in the aforesaid extraction procedure A was dissolved in 99.5% ethanol (400 ml) to carry out alcohol extraction. The alcohol solution thus formed was centrifuged at 4° C. and at 3000 rpm (Beckman Avanti™ J-30I) for 12 minutes to give a supernatant portion and a precipitate portion. The supernatant portion was further subjected to lyophilization using a Virtis apparatus to obtain a further purified alcohol extract in the form of lyophilized powder, which was called "TS 5-2" (also identified as "TSL-2").

100 g of extract "TSL-1" which was processed using the above procedure can yield approximately 1 g of "TS 5-2" in lyophilized powder form.

Extraction Procedure C

The precipitate portion obtained in the aforesaid extraction procedure B was lyophilized using a Virtis apparatus, and was subsequently dissolved in 50% ethanol. The 50% ethanol solution thus formed was centrifuged at 4° C. and at 3000 rpm (Beckman Avanti™ J-30I) for 12 minutes to give a supernatant portion and a precipitate portion. The supernatant portion was further subjected to lyophilization using a Virtis apparatus to obtain an extract in the form of lyophilized powder, which was called "TS 5—5" (also identified as "TSL-3).

Extraction Procedure D

The precipitate portion obtained in the aforesaid extraction procedure C was lyophilized using a Virtis apparatus, and was subsequently dissolved in 25% ethanol. The 25% ethanol solution thus formed was centrifuged at 4° C. and at 3000 rpm (Beckman Avanti™ J-30I) for 12 minutes to give a supernatant portion and a precipitate portion. Then, the supernatant portion and the precipitate portion were respectively lyophilized using a Virtis apparatus to obtain two extract products in lyophilized powder form, namely, "TSL-4" and "TSL-4P".

Extraction Procedure E

The extract product "TSL-4P" obtained in the aforesaid extraction procedure D was dissolved in RO water. The aqueous solution thus formed was centrifuged at 4° C. and at 3000 rpm (Beckman Avanti™ J-30I) for 12 minutes to give a supernatant portion and a precipitate portion. Then, the supernatant portion and the precipitate portion were respectively lyophilized using the Virtis apparatus to obtain two extract products in lyophilized powder form, which are respectively called "TS-H$_2$O-1" (also identified as "TSL-5") and "TSL-5P".

Extraction Procedure F

The extract product "TSL-5P" obtained in the aforesaid extraction procedure E was dissolved in RO water. The aqueous solution thus formed was centrifuged at 4° C. and at 3000 rpm (Beckman Avanti™ J-30I) for 12 minutes to give a supernatant portion and a precipitate portion. Then, the supernatant portion and the precipitate portion were respectively lyophilized using a Virtis apparatus to obtain two extract products in lyophilized powder form, namely, "TS5-4R" (also identified as "TS-H$_2$O-2" or "TSL-6") and "TSL-7",.

EXAMPLE 2

HPLC Analysis of Extract from Leaves of *Toona sinensis*

To understand the distribution of the major components of the extracts obtained from the leaves of *Toona sinensis* using the process according to the present invention, extracts "TS 5-4" and "TS 5-2", which were respectively obtained in extraction procedures A and B, were subjected to HPLC analysis.

Method:

In this example, the HPLC analyzer consisted of a Hitachi L-7100 pump, an L-7420 uv/vis detector, and a D-2410 degaser. The analysis software program was D-7000 HPLC System Manager. The analytical column was Mightysil RP-18 GP 250–4.6 (5 μm). The analytical conditions were: gradient solvent A: methanol; B: water; 0–10 min 20%–50% A; 10–20 min 50%–70% A; 20–40 min 70% A; flow rate 1 ml/min; wavelength 254 nm.

Figure 2:
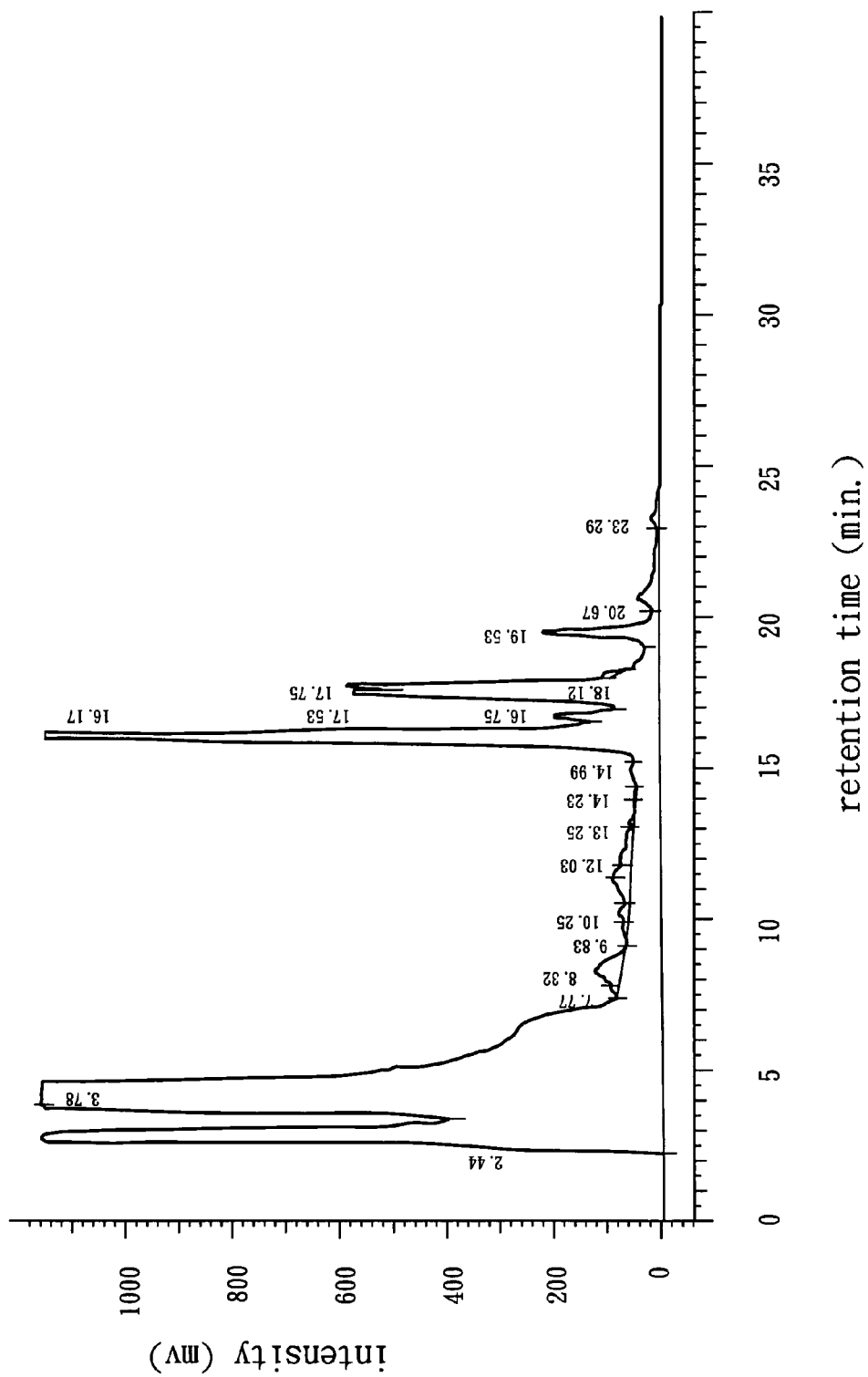
FIG. 2 is an HPLC elution profile of an alcohol-extracted extract (i.e., "TS 5-2" obtained in Example 1 below) obtained from the leaves of *Toona sinensis* according to a preferred embodiment of a process of the present invention.

Result:

FIGS. 1 and 2 respectively show HPLC elution profiles for "TS 5-4" and "TS 5-2". It is evident from a comparison of FIGS. 1 and 2 that, under the same separation conditions, the major compounds contained in "TS 5-4" and "TS 5-2" are different. Similar compound peaks were observed for "TS 5-4" and "TS 5-2" at the retention time points of 5 min, 16 min and 18 min. Most of the compounds contained in "TS 5-2" appeared in the first 3–4 peaks, and for "TS 5-4,"2–3 additional peak signals were observed at the retention time points of 25 min and 26 min.

EXAMPLE 3

XTT Cell Proliferation Assay for Extract from Leaves of *Toona sinensis*

To screen extracts from the leaves of *Toona sinensis* so as to determine whether they have anti-cancer cell activity, XTT cell proliferation assay was employed in this example, and a bladder cancer cell line, T24, purchased from the American Type Culture Collection (ATCC) (P.O. Box 1549, Manassas, Va. 20108, U.S.A.) was used to assay the five *Toona sinensis* leaf extracts obtained in Example 1, namely, "TS 5-4", "TS 5-2", "TS 5-5", "TS 5-5R", and "TS 5-4R".

Method:

The extracts obtained from the leaves of *Toona sinensis* in Example 1, namely, "TS 5-4", "TS 5-2", "TS 5-5", "TS 5-5R", and "TS 5-4R", were subjected to XTT cell proliferation assay (Roche Molecular Biochemicals). Each of the extracts was tested in concentrations of 1, 10 and 100 μg/mL, with H$_2$O, 50% EtOH and 99.5% EtOH as control groups.

The T24 bladder cancer cell line was cultured in a DMEM-F12 medium supplemented with 10% fetal calf serum (FCS), 10,000 unit/mL penicillin, 10 mg/mL streptomycin, and 0.025 mg/mL Amphotericin B.

The XTT cell proliferation assay (Roche) was performed in the following manner: cells were inoculated in a concentration of $5\times10^3$ cells/100 μl/well in a 96-well culture plate, and the culture plate was placed in an incubator containing 5% $CO_2$ for incubation for 24 hours. Thereafter, 1 μl of different *Toona sinensis* extracts, in PBS, was added to the cultured T24 cells to a final concentration of 100 μg/mL, 10 μg/mL or 1 μg/mL. 1 μl of H$_2$O, 50% EtOH or 99.5% EtOH was added to the cultured T24 cells, as control groups. After incubation for 72 hours, the culture medium was removed, and 100 μl of fresh culture medium and a pre-formulated 50 μl XTT mixed reagent (XTT reagent: electronically coupled reagent=50:1)were added. The culture plate was placed in the incubator for 4 hours. Thereafter, the light absorbence values (OD=OD$_{492}$–OD$_{690}$) were read at wavelengths of 492 nm and 690 nm using an ELISA reader for calculating the inhibitory concentration 50% (IC$_{50}$), i.e., the cell concentration at which the light absorbence value of the experimental group is one half of that of the control group.

Figure 3:
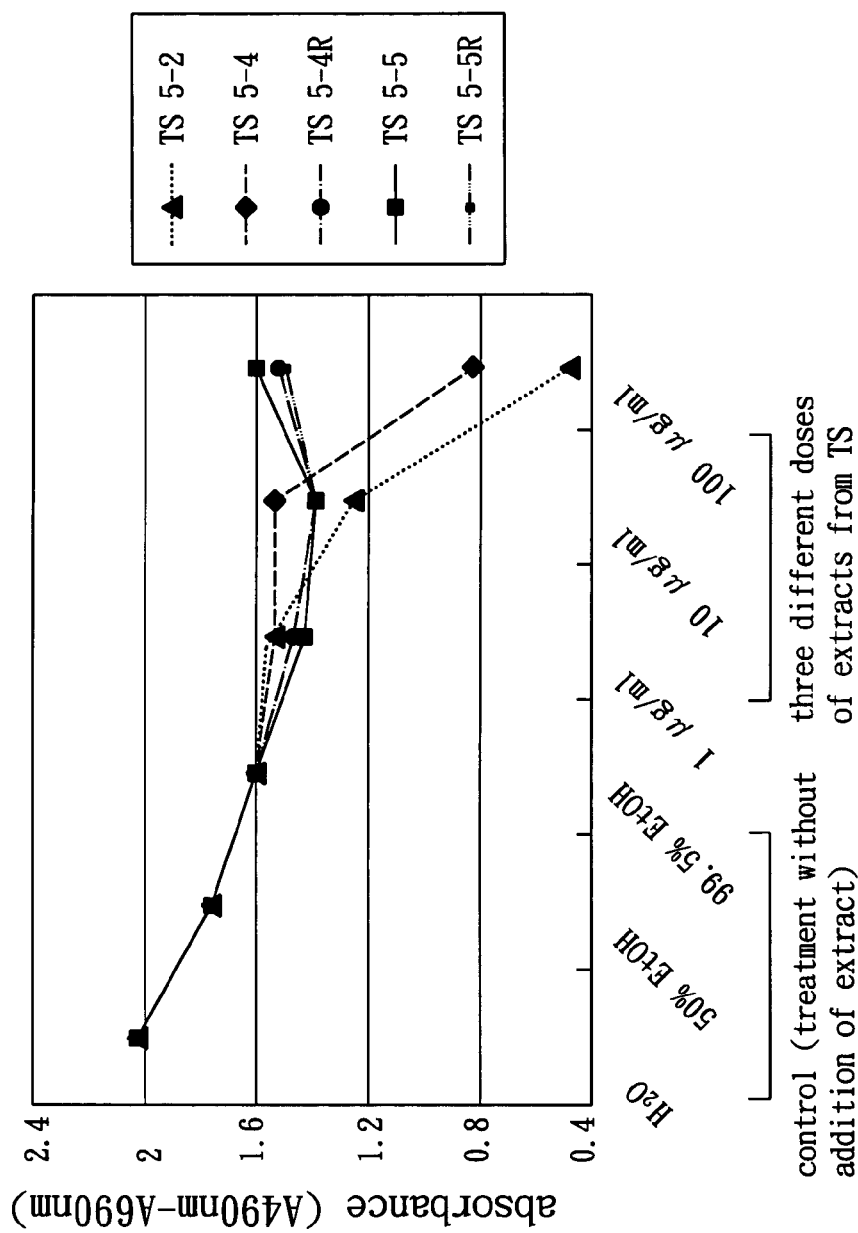
FIG. 3 shows the cytotoxicity effects of five different extracts, which were obtained from the leaves of *Toona sinensis* (TS) by employing different purification treatments, on a bladder cancer cell line, T24, wherein solvents used in the extraction of the leaves of *Toona sinensis* are water, 50% EtOH and 99.5% EtOH, which also serve as control groups.

Result:

FIG. 3 shows the results of the XTT cell proliferation assay of the five extracts, i.e., "TS 5-4", "TS 5-2", "TS 5-5", "TS 5-5R", and "TS 5-4R," obtained from the leaves of *Toona sinensis* in Example 1, wherein the lower the absorbence values, the fewer in number are the surviving cells. It is clear from FIG. 3 that "TS 5-2" has the highest cytotoxicity on the T24 bladder cancer cell line, with "TS 5-4" second thereto. Furthermore, the cytotoxicity of "TS 5-2" on the T24 bladder cancer cell line was dosage dependent, and the IC$_{50}$ found by calculation was 71.3 μg/mL.

EXAMPLE 4

Effects of Extracts from Leaves of *Toona sinensis* on Cell Cycle

This example investigated the effect of "TS 5-2" on the cell cycle of the T24 bladder cancer cell line. Different doses of "TS 5-2" were used to treat unsynchronized bladder cancer cells for 24 hours, which were then subjected to fluorescence-activated cell sorter (FACS) analysis to evaluate cell cycle changes.

Method:

Cancer cells in a concentration of $2\times10^5$ cells/plate were inoculated into 6 cm culture plates and cultured for 24 hours. Then, the culture medium was replaced with a culture medium containing 1, 10 or 100 μg/mL "TS 5-2, " and the cells were cultured for another 24 hours. Thereafter, the culture plates were treated with trypsin, with the culture medium neutralizing the collected cells. Centrifugation was performed at 1500 rpm for 5 minutes to remove the supernatant. 300 μl of PBS was added to disperse the cells homogeneously, and 700 μl of 99.5% alcohol was added slowly to fix the cells. The cells were allowed to react at 4° C. for 30 minutes, and were further subjected to centrifugation to remove the supernatant. PBS containing 0.1% triton and 0.05% RNase was added. After the cells were allowed to react at 37° C. for 1 hour, centrifugation was performed once again to remove the supernatant, and PBS containing 40 μg/mL of propidium iodide was added. After standing the cells in darkness at 4° C. to react for 30 minutes, dispersal and screening were performed using a 60 μm mesh filter for subsequent analysis by flow cytometry.

Result:

Referring to Table 1 below, the inventors found that the T24 bladder cancer cells at G2 phase increased after being treated with "TS 5-2", especially when 100 μg/mL was used. As use of medicaments that would target cells at different cell cycle phases in a combination therapy is a standard form of cancer treatment, the results shown in FIG. 2 provide useful information on the clinical application of the *Toona sinensis* leaf extracts according to the present invention.

TABLE 1

| | Percentage of cells at each cell cycle phases 24 hours after the cells were treated with "TS 5-2" | | |
|---|---|---|---|
| Dosage | G1 | S | G2 |
| Control group | 45 | 14.1 | 40.9 |
| 100 μg/mL | 8.6 | 27.9 | 63.5 |
| 10 μg/mL | 33.7 | 13.6 | 52.8 |
| 1 μg/mL | 43.9 | 13.2 | 42.9 |

EXAMPLE 5

In Vitro Anti-cancer Cell Test of Extracts from Leaves of *Toona sinensis*

In this embodiment, "TS 5-2" was further used to treat several cancer cells from the urogynecological system, including two ovarian cancer cell lines, SKOV3 and PA-1, two cervical cancer cell lines, HeLa and HeLa S3, and an endometrial cancer cell line, RL95-2, so as to study the cytotoxicity of "TS5-2" on the aforesaid cancer cell lines.

Origin and Culture of Cancer Cell Lines:

The cancer cell lines, SKOV 3, PA-1, HeLa, HeLaS3, and RL95-2, which were used in this embodiment were purchased from ATCC, and were cultured in a DMEM-F12 medium supplemented with 10% fetal calf serum (FCS), 10,000 unit/mL penicillin, 10 mg/mL streptomycin, and 0.025 mg/mL Amphotericin B.

Method:

Cancer cells in a concentration of $15 \times 15^5$ cells/plate were inoculated in a 10 cm culture plate for culturing overnight. Then, the culture medium was replaced with a culture medium containing 1 mg/mL "TS 5-2" ("TS 5-2" was pre-dissolved in PBS for concentration adjustment), and culture of the cells was continued for 24 or 48 hours. Thereafter, trypsin (0.05% trypsin/0.02% EDTA in PBS) was used to treat the culture plate, and the harvested cells were placed in a microtube, which was then placed in an ice bath. The cells were suspended in a suspension (0.05% trypsin/0.02% EDTA in PBS) and mixed homogeneously with trypan blue at a ratio of 1:1. Then, the number of viable cells was counted using a hemacytometer under a microscope (Nikon TS100).

Figure 4:
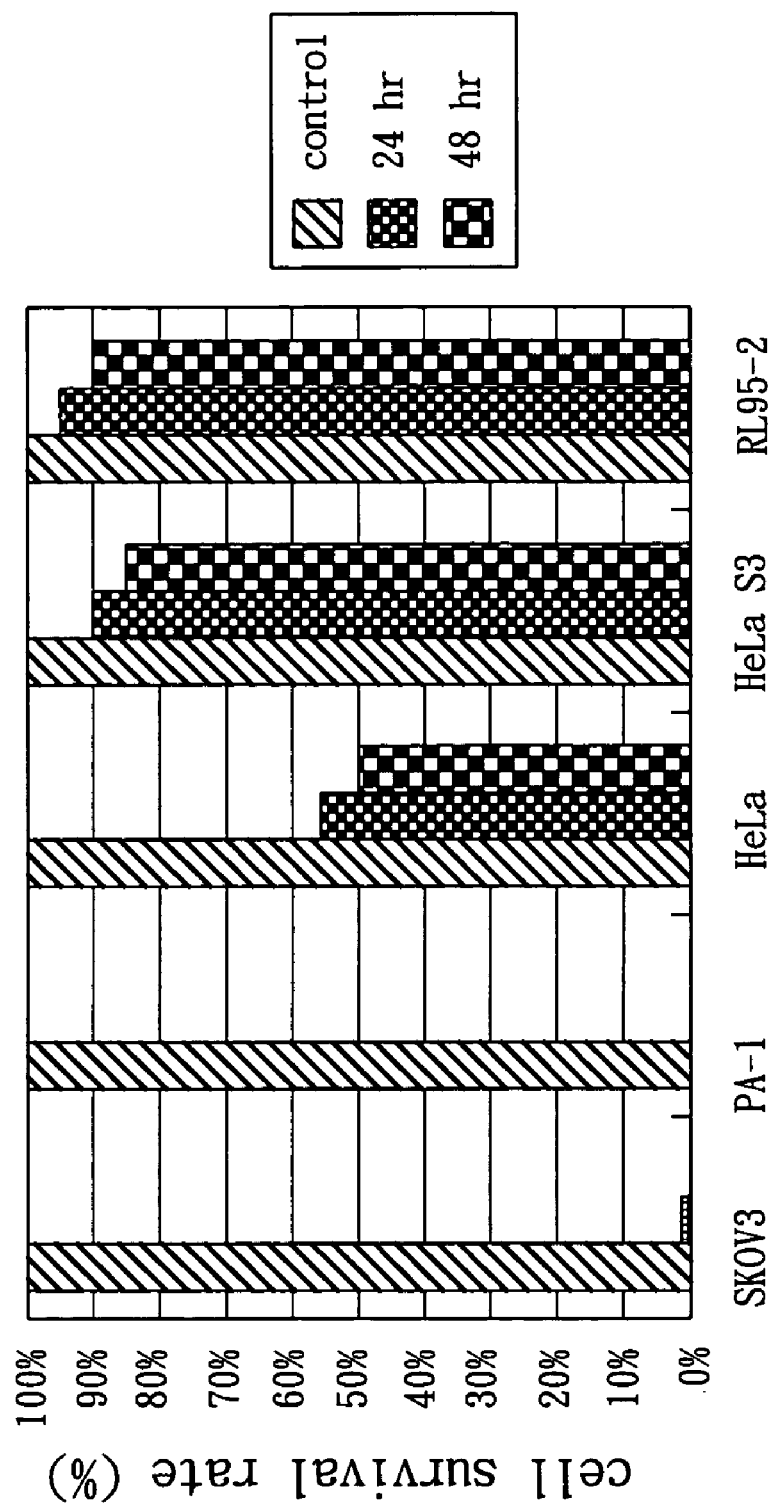
FIG. 4 shows the effects of the extract from the leaves of *Toona sinensis* (i.e., "TS 5-2"), which was obtained according to the preferred embodiment of the process of the present invention, on the suppression of growth of different cancer cell lines, wherein the control group is an experimental group not added with any extract from the leaves of *Toona sinensis*.

Result:

To further determine the cytotoxicity of "TS 5-2" on the cancer cells of the urogynecological system, "TS 5-2" in a concentration of 1 mg/mL was used to treat the SKOV3 and PA-1 ovarian cancer cell lines, the HeLa and HeLaS3 cervical cancer cell lines, and the RL95-2 endometrial cancer cell line for 24 hours or 48 hours. The results are shown in FIG. 4 in comparison with the control group, to which "TS 5-2" was not added. The coordinate indicates the rate (%) of cell viability compared to the control group.

It is apparent from FIG. 4 that "TS 5-2" in a concentration of 1 mg/mL already exhibited a potent growth inhibiting effect on the SKOV3 and PA-1 ovarian cancer cell lines after 24 hours of treatment (almost completely stopped growth of the cancer cells). For the RL95-2 endometrial cancer cell line and the HeLaS3 cervical cell line, the cancer cell growth inhibitory effect exhibited by "TS 5-2" after 48 hours of treatment was not very strong. For the HeLa cervical cancer cell line, "TS 5-2" exhibited 50% cancer cell growth inhibitory effect after 48 hours of treatment.

Table 2 below shows the $IC_{50}$ values of "TS 5-2" for each of the five cancer cell lines, wherein the calculation of $IC_{50}$ values was based on the concentration of the extract 48 hours after introduction, at which 50% of the cells were viable (taking the total count of viable cells in the control group as 100%). As shown in Table 2, the $IC_{50}$ values of "TS 5-2" on the SKOV3 and PA-1 ovarian cancer cell lines are, respectively, 28 μg/mL and 10 μg/mL. These data indicate that "TS 5-2" has the potential to be developed into an effective anti-ovarian cancer drug.

TABLE 2

| Cancer cell line | $IC_{50}$ |
|---|---|
| SKOV3 | 28 μg/mL |
| PA-1 | 10 μg/mL |
| HeLa | 1 mg/mL |
| HeLa S3 | >1 mg/mL |
| RL95-2 | >1 mg/mL |

EXAMPLE 6

Effect of Extracts from Leaves of *Toona sinensis* on Cell Morphology and Cell Cycle of Ovarian Cancer Cells This example further investigates changes in cell morphology and cell cycle of ovarian cancer cells after the latter are subjected to action of the extract prepared from the leaves of *Toona sinensis* according to the present invention.

Method:

With reference to the method described in Example 5, the SKOV3 and PA-1 ovarian cancer cell lines were cultured in a culture plate, treated with "TS 5-2" of 1 mg/mL, 100 μg/mL and 10 μg/mL, respectively, and observed for changes in cell morphology under a microscope.

In addition, with reference to the method described in Example 4, the SKOV3 ovarian cancer cell line was cultured in a culture plate, treated with 100 μg/mL and 10 μg/mL of "TS 5-2, " respectively, and subjected to FACS analysis.

Figure 5:
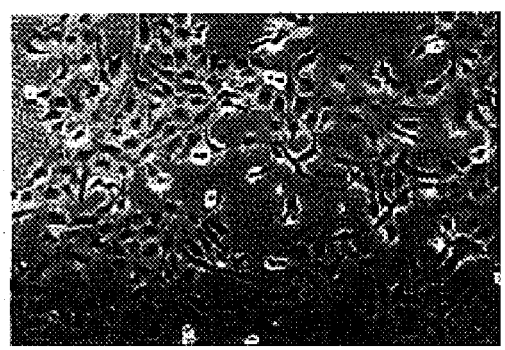
FIG. 5 shows the cell morphology effects of different concentrations (1 mg/ml, 100 μg/ml) of the extract from the leaves of *Toona sinensis* (i.e., "TS 5-2"), which was obtained according to the preferred embodiment of the process of the present invention, on an ovarian cancer cell line, SKOV3, wherein the control group is an experimental group not added with any extract from the leaves of *Toona sinensis*.
Figure 5:
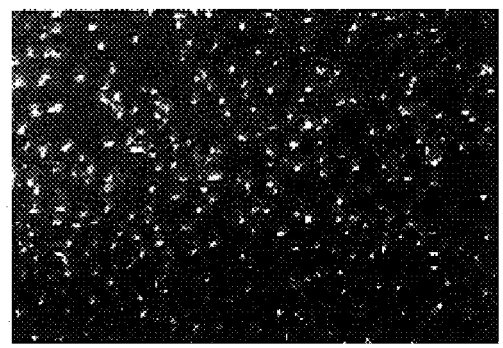
Figure 5:
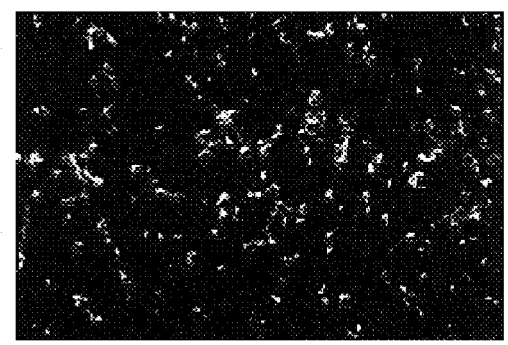
Figure 6:
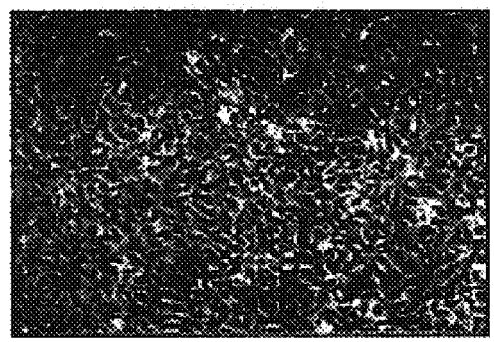
FIG. 6 shows the cell morphology effects of different concentrations (1 mg/ml, 10 μg/ml) of the extract from the leaves of *Toona sinensis* (i.e., "TS 5-2"), which was obtained according to the preferred embodiment of the process of the present invention, on an ovarian cancer cell line, PA-1, wherein the control group is an experimental group not added with any extract from the leaves of *Toona sinensis*.
Figure 6:
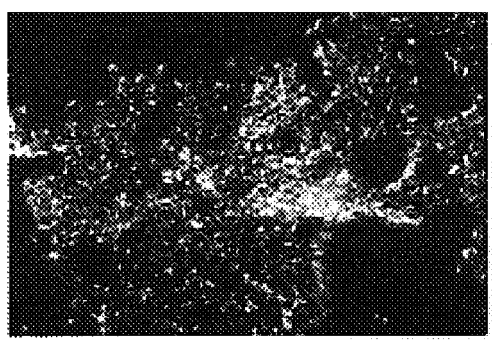
Figure 6:
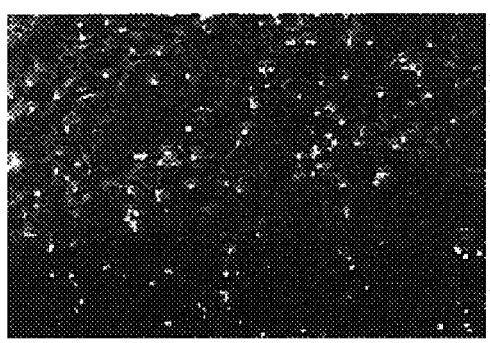

Result:

FIGS. 5 and 6 respectively show the morphological effect of "TS 5-2" on the SKOV3 and PA-1 ovarian cancer cell lines at different doses. As shown in FIGS. 5 and 6 (under 100× amplification), after 24-hour treatment with a dose of 1 mg/mL, "TS 5-2" initiated apoptosis and cell floating in a large number of cells. Treatment with "TS 5-2" for 24 hours at respective doses of 100 μg/mL and 10 μg/mL still resulted in obvious cell death in the SKOV3 and PA-1 ovarian cancer cell lines.

In addition, after the SKOV3 ovarian cancer cell line was treated with "TS 5-2" for 24 hours at different doses, the cell cycle distribution of the SKOV3 ovarian cancer cell line was observed using FACS analysis. The results are shown in Table 3.

TABLE 3

| Dosage | Percentage (means ± SD) of cervical cancer cells at each cell cycle phase after treatment with "TS 5-2" for 24 hours | | |
|---|---|---|---|
| | G1 | S | G2/M |
| Control group | 59.0 ± 0.2 | 27.3 ± 0.9 | 13.8 ± 0.7 |
| 10 µg/mL | 53.7 ± 1.3 | 32.1 ± 1.4 | 14.2 ± 1.1 |
| 100 µg/mL | 54.2 ± 1.6 | 20.9 ± 0.9 | 25.0 ± 2.5 |

The SKOV3 ovarian cancer cell line was assessed using cell survival assay after being treated with "TS 5-2" for 4 hours. It was found that "TS 5-2" had an enhanced cell cytotoxicity on the SKOV3 ovarian cancer cell line at M phase (Table 4).

TABLE 4

| SKOV3 | | Viable cells (number) | Dead cells (number) | Apoptotic cells(%) |
|---|---|---|---|---|
| 8 hr | No treatment for 4 hr. | 83 | 1 | 1.2 |
| 8 hr | 1 mg/ml TS treatment for 4 hr | 157 | 12 | 7.1 |
| 12 hr | No treatment for 4 hr. | 77 | 1 | 1.3 |
| 12 hr | 1 mg/ml TS treatment for 4 hr. | 72 | 9 | 11.1 |
| 16 hr | No treatment for 4 hr. | 113 | 3 | 2.6 |
| 16 hr | 1 mg/ml TS treatment for 4 hr. | 59 | 3 | 4.8 |
| 20 hr | No treatment for 4 hr. | 80 | 2 | 2.4 |
| 20 hr | 1 mg/ml TS treatment for 4 hr. | 82 | 6 | 6.8 |
| 24 hr | No treatment for 4 hr. | 104 | 8 | 7.1 |
| 24 hr | 1 mg/ml treatment for 4 hr. | 88 | 14 | 13.7 |
| M phase | No treatment for 4 hr. | 91 | 9 | 9.0 |
| M phase | 1 mg/ml TS treatment for 4 hr. | 78 | 36 | 31.6 |

Note:
"TS" stands for "TS 5-2."

The results in Tables 3 and 4 indicate that "TS 5-2" increased retention of the SKOV3 ovarian cancer cell line at G2/M phase, and exhibited higher cytotoxicity on the SKOV3 ovarian cancer cell line at M phase.

EXAMPLE 7

Test of Extract of Leaves of *Toona sinensis* in Animal Model In Vivo

To verify whether the extract of leaves of *Toona sinensis* according to the present invention can exert an anti-cancer effect in vivo, nude mice were used as an in vivo animal model in this example.

Method:

$2 \times 10^5$ SKOV3 cells/0.1 mL PBS was inoculated subcutaneously into the back of 5–6 week old male nude mice (Foxnlnu/Foxnlnu n=5) of 24–29 g. After development of tumors of at least 3 mm (which took about 1 week), the nude mice were administered with "TS 5-2" by intraperitoneal injection and observed.

In this example, "TS 5-2" was prepared in the following manner: "TS 5-2" was dissolved in PBS, filtered, and formulated into 67.25 mg/mL and 672.5 mg/mL. Then, "TS 5-2" was administered to each nude mouse according to its weight (dose: 0.6725 µg/g of weight of the mouse or 6.725 µg/g of weight of the mouse).

Result:

Male nude mice having significant lumps of tumor resulting from subcutaneous injection of the SKOV3 ovarian cancer cell line ($2 \times 10^5$ cells) were administered with a low dose of "TS 5-2" at 0.67 µg/g or with a high dose at 6.7 µg/g five days a week for a period of seven weeks.

Anatomical examination revealed that the tumors in the nude mice of the experimental group which were administered with a high dose of "TS 5-2" (6.7 µg/g) significantly shrank to an extent that they almost disappeared, and that those in the experimental group which were administered with a low dose (0.67 µg/g) also exhibited shrinkage in the size of the tumors. As for the nude mice in the control group, which were administered with PBS by injection, the tumors grew significantly. Compared with the control group treated with PBS, it is evident that "TS 5-2" administered by intraperitoneal injection suppressed growth of tumor in a dosage-dependent relationship.

Figure 7:
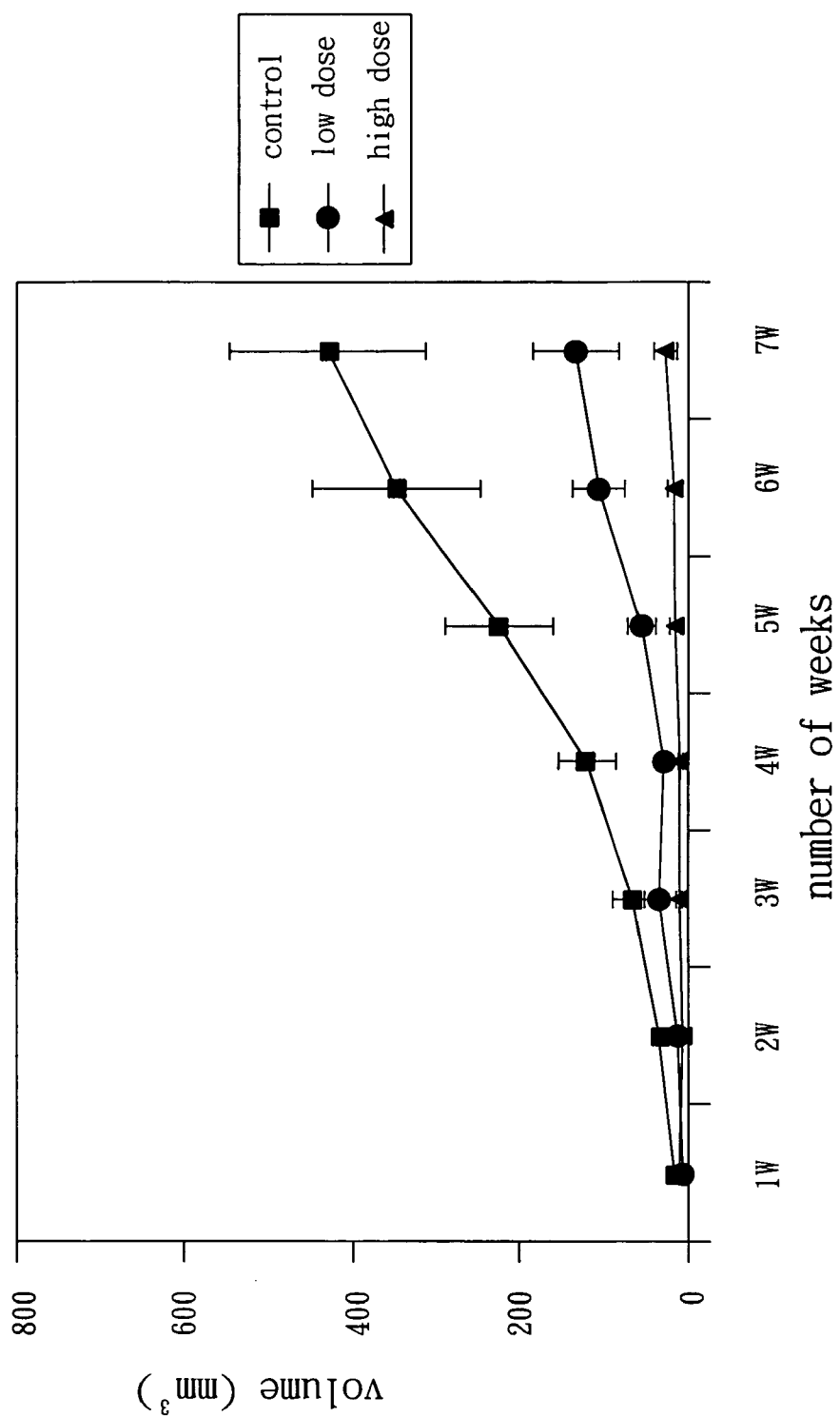
FIG. 7 shows the changes in size of tumors grown from ovarian cancer cells injected into nude mice after the nude mice were administered with low and high doses of the extract obtained from the leaves of *Toona sinensis* (i.e., "TS 5-2") according to the preferred embodiment of the process of the present invention, wherein the size of the tumors was measured once a week for a period of 7 weeks.

FIG. 7 illustrates the changes in size of the tumors in the nude mice after seven weeks of observation. Particularly, the lumps of tumor in the nude mice administered with a high dose of "TS 5-2" almost vanished. Moreover, referring to FIG. 5, after intraperitoneal injection of "TS 5-2" for a period of seven weeks, no significant toxicity to the bone marrow, kidneys or liver of the nude mice was observed.

TABLE 5

| Means ± SD | Control group | Low dose | High dose |
|---|---|---|---|
| WBC ($10 * 3/\mu l$) | 3.32 ± 0.88 | 3.143 ± 0.67 | 4.562 ± 1.14 |
| RBC ($10 * 6/\mu l$) | 9.34 ± 0.17 | 9.21 ± 0.41 | 9.755 ± 0.19 |
| HGB (g/dl) | 12.45 ± 0.20 | 12.5 ± 0.42 | 13.525 ± 0.32 |
| HCT (%) | 41.5 ± 0.76 | 41.266 ± 1.83 | 44.85 ± 0.91 |
| MCV (fl) | 44.45 ± 0.65 | 44.833 ± 0.50 | 46 ± 0.79 |
| MCH (pg) | 13.33 ± 0.14 | 13.6 ± 0.15 | 13.875 ± 0.13 |
| MCHC (%) | 30.05 ± 0.61 | 30.333 ± 0.39 | 30.15 ± 0.33 |
| BUN (mg/dL) | 29.3 ± 2.3 | 28.0 ± 2.0 | 25.0 ± 4.0 |
| (Creatinine) (mg/dL) | 0.43 ± 0.11 | 0.47 ± 0.04 | 0.47 ± 0.16 |
| AST (IU/L) | 101.3 ± 23.3 | 111.7 ± 24.3 | 150.0 ± 30.7 |
| ALT (IU/L) | 29.8 ± 17.7 | 48.0 ± 20.0 | 60.7 ± 51.4 |

The above experimental results clearly indicate that extracts from the leaves of *Toona sinensis* are highly promising anti-ovarian cancer drugs.

All patents and literature references cited in the present specification are hereby incorporated thereinto by reference in their entirety. In case of conflict, the present description, including definitions, shall prevail.

While the invention has been described with reference to the above specific embodiments, it is apparent that numerous modifications and variations can be made without departing from the scope and spirit of this invention. It is therefore intended that this invention be limited only as indicated by the appended claims.

We claim:

1. An extract from leaves of *Toona sinensis*, which is prepared by a process comprising the following steps:
   (a) extracting the leaves of *Toona sinensis* with water by heating to obtain an aqueous extract solution;
   (b) drying the aqueous extract solution obtained in step (a) to obtain a dried first extract;

(c) dissolving the first extract obtained in step (b) in an alcohol solvent to form an alcohol extract solution; and (d) removing the alcohol solvent from the alcohol extract solution obtained in step (c) to obtain a dried second extract;

wherein the extract is suitable for inhibiting growth of a cancer cell selected from the group consisting of ovarian cancer cell and bladder cancer cell.

2. The extract from leaves of *Toona sinensis* as claimed in claim 1, which is adapted for use in the preparation of a medicament for treating ovarian cancer or bladder cancer.

3. A process for preparing an extract from leaves of *Toona sinensis*, comprising the following steps:

(a) extracting the leaves of *Toona sinensis* with water by heating to obtain an aqueous extract solution;

(b) drying the aqueous extract solution obtained in step (a) to obtain a dried first extract;

(c) dissolving the first extract obtained in step (b) in an alcohol solvent to form an alcohol extract solution; and (d) removing the alcohol solvent from the alcohol extract solution obtained in step (c) to obtain a dried second extract;

wherein the extract is suitable for inhibiting growth of a cancer cell selected from the group consisting of ovarian cancer cell and bladder cancer cell.

4. The process as claimed in claim 3, wherein, in step (a), the aqueous extract solution is obtained by boiling down water added with the leaves of *Toona sinensis* to an appropriate amount for subsequent filtering.

5. The process as claimed in claim 4, wherein filtering is conducted by using an apparatus selected from the group consisting of gauze, cotton wool, a filter sieve with a predetermined mesh, and a combination thereof.

6. The process as claimed in claim 3, wherein the drying treatment employed in step (b) is selected from the group consisting of lyophilization, low-temperature spray-drying, low-temperature evaporation, and a combination thereof.

7. The process as claimed in claim 6, wherein the drying treatment employed in step (b) is lyophilization.

8. The process as claimed in claim 3, wherein step (b) includes the following sub-steps:

(i) centrifuging the aqueous extract solution obtained in step (a) to obtain a supernatant and a precipitate; and (ii) subjecting the supernatant obtained in step (i) to a drying treatment.

9. The process as claimed in claim 8, wherein the drying treatment employed in step (ii) is selected from the group consisting of lyophilization, low-temperature spray-drying, low-temperature evaporation, and a combination thereof.

10. The process as claimed in claim 3, wherein the alcohol employed in step (c) is selected from the group consisting of ethanol, methanol, propanol, isopropanol, n-butanol, isobutanol, and a combination thereof.

11. The process as claimed in claim 10, wherein the alcohol employed in step (c) is ethanol.

12. The process as claimed in claim 3, wherein the removal of the alcohol solvent in step (d) is performed by using a method selected from the group consisting of lyophilization, evaporation, spray-drying, and a combination thereof.

13. The process as claimed in claim 12, wherein step (d) is carried out by using lyophilization.

14. A pharmaceutical composition, comprising:

(a) a therapeutically effective amount of an extract from leaves of *Toona sinensis* prepared according to the process of claim 3; and (b) a pharmaceutically acceptable carrier;

wherein the composition is suitable for inhibiting growth of a cancer cell selected from the group consisting of ovarian cancer cell and bladder cancer cell.

15. The pharmaceutical composition as claimed in claim 14, which is adapted for use in the treatment of cancer selected from ovarian cancer and bladder cancer.

16. A pharmaceutical composition for inhibiting growth of a cancer cell selected from the group consisting of ovarian cancer cell and bladder cancer cell, comprising:

(a) a therapeutically effective amount of an extract prepared from leaves of *Toona sinensis* by the process according to claim 3; and (b) a pharmaceutically acceptable carrier.

17. A pharmaceutical composition for treating bladder cancer comprising:

(a) a therapeutically effective amount of an extract from leaves of *Toona sinensis* selected from either one of:

(i) the extract from leaves of *Toona sinensis* according to claim 1;

(ii) an extract from leaves of *Toona sinensis* prepared by the process according to claim 3; and (b) a pharmaceutically acceptable carrier.

* * * * *